US011678105B2

(12) United States Patent
Hoang Co Thuy

(10) Patent No.: US 11,678,105 B2
(45) Date of Patent: Jun. 13, 2023

(54) NOISE CANCELING HEADPHONES

(71) Applicant: DEVIALET, Paris (FR)

(72) Inventor: Vu Hoang Co Thuy, Paris (FR)

(73) Assignee: DEVIALET, Paris (FR)

(*) Notice: Subject to any disclaimer, the term of this patent is extended or adjusted under 35 U.S.C. 154(b) by 0 days.

(21) Appl. No.: 17/490,636

(22) Filed: Sep. 30, 2021

(65) Prior Publication Data

US 2022/0124431 A1 Apr. 21, 2022

(30) Foreign Application Priority Data

Oct. 1, 2020 (FR) ..................................... 20 10064

(51) Int. Cl.

| | |
|---|---|
| ***A61F 11/06*** | (2006.01) |
| ***H04R 1/10*** | (2006.01) |
| ***G10K 11/178*** | (2006.01) |
| *G10K 11/16* | (2006.01) |

(52) U.S. Cl.
CPC ..... *H04R 1/1083* (2013.01); *G10K 11/17813* (2018.01); *G10K 2210/1081* (2013.01); *H04R 2460/01* (2013.01)

(58) Field of Classification Search
CPC .............. H04R 1/1083; H04R 2460/01; G10K 11/17813; G10K 2210/1081
USPC ......................................... 381/71, 71.1, 71.6
See application file for complete search history.

(56) References Cited

U.S. PATENT DOCUMENTS

| | | | | |
|---|---|---|---|---|
| 2008/0112569 | A1 | 5/2008 | Asada | |
| 2009/0080670 | A1 | 3/2009 | Solbeck et al. | |
| 2010/0274369 | A1* | 10/2010 | Kanishima | H04R 1/1083 700/94 |
| 2017/0270905 | A1 | 9/2017 | Asada | |
| 2018/0068649 | A1 | 3/2018 | Asada | |
| 2019/0251946 | A1 | 8/2019 | Asada | |

OTHER PUBLICATIONS

Preliminary Search Report dated May 31, 2021 in French Application No. 2010064.

* cited by examiner

*Primary Examiner* — Ammar T Hamid
(74) *Attorney, Agent, or Firm* — B. Aaron Schulman, Esq.; Stites & Harbison, PLLC

(57) ABSTRACT

The headphones (10) comprise:
a transducer (16) (12);
an noise-canceling processing chain (30, 40) comprising:
a microphone (31, 41);
a noise-canceling processing filter (34, 44) which comprises in series:
a stabilisation filter (34A, 44A) whose transfer function is substantially equal to the inverse of the transfer function of the processed secondary path, and
a noise cancellation filter (34B, 44B) whose transfer function is a noise cancellation transfer function.
The secondary path is formed between the transducer (16) and the eardrum, and
the transfer function of the processed secondary path is the transfer function of the secondary path combined with the transfer functions of the processing components, excluding the processing filter (34, 44).

5 Claims, 3 Drawing Sheets

NOISE CANCELING HEADPHONES

The present invention relates to a noise-canceling headset of the type comprising:

an electro-acoustic transducer placed in a sound reproduction cavity;

at least one noise-canceling chain comprising:

a microphone to capture ambient sound;

a noise-canceling filter to process the signal from the microphone to produce a noise-canceling signal;

means for applying the noise-canceling signal to drive the electro-acoustic transducer.

The noise-cancelling headset comprises at least one microphone placed either inside the cavity between the electro-acoustic transducer and the ear canal or outside the cavity. Ideally, such a headset has microphones placed in both positions.

To ensure that a noise-canceling signal is created and reproduced by the transducer, the signals from the two microphones are processed by digital filters, which may be a combination of one or more filters.

Headsets with internal microphones generally perform well in terms of noise reduction levels, typically on the order of 20-30 dB, but in a limited frequency range, typically 50-1000 Hz, due to the instability of the feedback loop formed by the internal microphone and its filter directly receiving the signals from the electro-acoustic transducer. This instability can cause audible feedback and the filters therefore have an inferred range of action to avoid this phenomenon.

External microphone headsets do not have this instability restriction in that there is only a highly attenuated signal on the order of 50 dB from the electro-acoustic transducer picked up by the external microphone, which does not create audible feedback. They generally provide attenuations of up to 10 dB, since the microphone favours a direction of external noise pick-up coming towards the ear.

External microphone noise-canceling headsets can theoretically attenuate noise above 1 kHz, but performance is highly dependent on the direction of the noise source, particularly at higher frequencies.

The filters used at the output of the external or internal microphones are designed to seek to avoid the problems previously mentioned, namely feedback for internal microphones and reduced performance due to the high directivity of the measurements in the case of an external microphone.

These filters are commonly defined empirically to modulate gain as a function of frequency.

The purpose of the invention is to provide a solution to this feedback problem for internal microphones, and the difficulty of constructing a filter that performs well with respect to directivity for external microphones while allowing the satisfactory frequency ranges of the noise reducer to be expanded.

To this end, the invention has as its object a noise-canceling headset of the aforementioned type, characterised in that, for the or each noise-canceling processing chain, the processing filter comprises in this order:

a stabilisation filter whose transfer function is substantially equal to the inverse of the transfer function of the processed secondary path, and a noise cancellation filter whose transfer function is a noise cancellation transfer function, the secondary path being formed between the electro-acoustic transducer and the users eardrum, and the transfer function of the processed secondary path being the transfer function of the secondary path combined with the transfer functions of the various components providing processing up to the transducer in the noise-cancellation processing chain, except for the processing filter.

In particular embodiments, the noise-cancelling headset comprises one or more of the following features:

the stabilisation filter is constructed so that its transfer function is substantially equal to the inverse of the transfer function of the processed secondary path, from 5 Hz to 50 Hz and from 1 kHz to 10 kHz, to within 5 dB of gain and with a phase shift of +45 to −45° on the corrected phase of the linear phase due to the pure delay resulting from propagation in air and from the delay due to the processor;

it comprises an internal noise-cancellation processing chain with an internal microphone placed in the sound reproduction cavity;

in the internal noise-cancellation processing chain, the noise cancellation transfer function has a gain greater than 20 dB over the entire audio range;

In the internal noise-cancellation processing chain, the stabilisation filter is a proportional-integral filter or a shelving filter;

it comprises an external noise-cancellation processing chain with an external microphone placed in the sound reproduction cavity;

in the external noise-cancellation processing chain, the noise cancellation transfer function is substantially equal to the opposite of the quotient of the transfer function corresponding to the passive attenuation of the cavity and the transfer function between the outer envelope of the cavity and the external microphone.

The invention also relates to a method of manufacturing a noise-canceling headset comprising:

an electro-acoustic transducer;

at least one noise-canceling chain comprising:

a microphone to capture ambient sound;

a noise-canceling filter to process the signal from the microphone to produce a noise-canceling signal;

means for applying the noise-canceling signal to drive the electro-acoustic transducer.

comprising, for the or each noise-canceling processing chain, the steps of:

1. measuring the transfer function of a processed secondary path;

the secondary path being formed between the electro-acoustic transducer and the users eardrum, and the transfer function of the processed secondary path being the transfer function of the secondary path combined with the transfer functions of the various components providing processing up to the transducer in the noise-cancellation processing chain, except for the processing filter 2. inverting the transfer function of a processed secondary path;

3. creating a processing filter with a transfer function formed from the product of:

the inverse of the transfer function of a processed secondary path, and a noise cancellation transfer function; and 4. constructing a headset whose noise-canceling filter is the created processing filter.

In particular embodiments, the method comprises measuring the transfer function of the processed secondary path on a complete headset but without the or each noise-canceling processing filter by exciting the transducer with a sinusoidal function of varying frequency over the entire audio range and measuring the resulting signal on an artificial ear.

The invention will be better understood upon reading the following description, given only as an example, and with reference to the drawings, in which:

FIG. 1 shows a schematic illustration of a set of noise-cancelling headphones 10.

Figure 1:
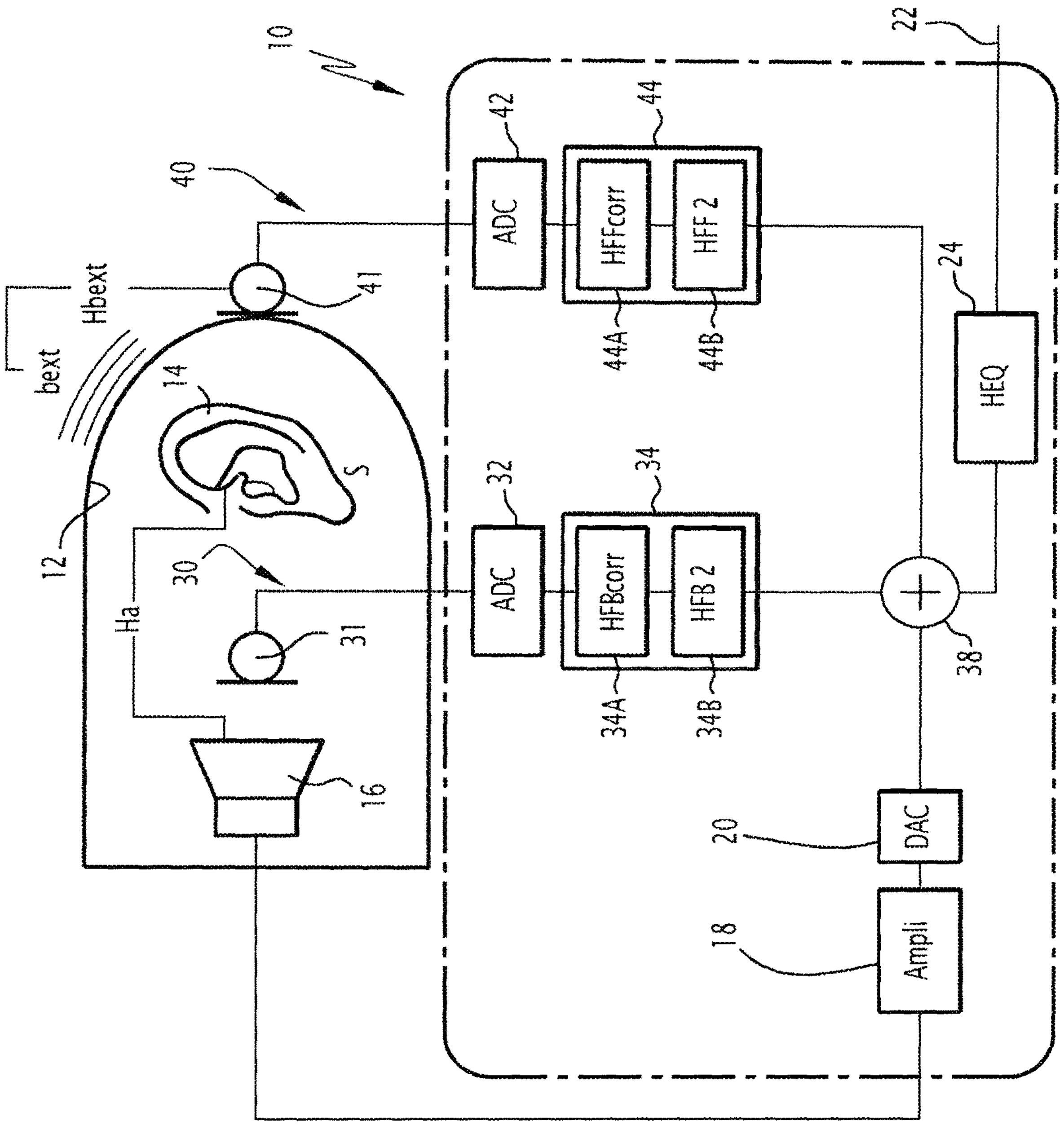
FIG. 1 is a schematic view of a noise-canceling headset according to the invention.

It comprises a sound reproduction cavity 12 inside which an ear 14 of the headset wearer is diagrammed.

As is known per se, this cavity comprises an electro-acoustic transducer 16 arranged opposite the ear canal. This cavity 12 is formed, for example, by a shell covering most of the ear in the case of external headphones, or takes the form of an anatomical housing that can be inserted into the entrance to the ear canal in the case of an in-ear headphone.

The transducer 16 is connected, for its excitation, to an amplifier 18, assumed to have a unitary gain, receiving a digital signal to be reproduced through a digital/analog converter 20.

The headphones have an input 22 for a music signal to be reproduced, which is connected to the input of the digital/analogue converter 20 through an equalisation filter 24.

In order to provide noise-canceling processing, the headset 10 comprises an internal noise-canceling processing chain 30 comprising an internal microphone 31 arranged inside the cavity 12 opposite the electro-acoustic transducer 16.

The external microphone 31 is suitable for picking up the sound produced by the transducer 16 and the external noise at the outer envelope of the cavity 12, denoted bext, filtered by the cavity 12 whose transfer function is denoted HPA.

The path formed between the transducer 16 and the users eardrum is called the "secondary path" and its transfer function is denoted Ha.

The transfer function between the measurement point of the internal microphone 31 and the eardrum is denoted Hmici-t. Thus the transfer function between the transducer 16 and the measurement point of the microphone 31 is equal to Ha/Hmici-t.

In practice, since the distance between the internal microphone 31 and the eardrum is very small, Hmici-t is approximately equal to 1. Accordingly, it is assumed in practice and in the remainder of this document that the transfer function of the secondary path and the transfer function between the transducer 16 and the internal microphone measurement point 31 are both equal to Ha.

The microphone 31 is connected, in the chain 30, to an internal signal processing filter 34, which provides a noise-canceling signal, with the interposition of an analog/digital converter 32.

The output of the internal processing filter 34 is connected to the amplifier 18 via a summing unit 38 upstream of the digital/analogue converter 20. This summing unit adds the equalised signals from the input 22 to the noise-canceling signals from the internal processing chain 30.

Similarly, the headset 10 has an external noise-cancellation system 40 with an external microphone 41 mounted outside the cavity 12.

The external microphone 41 is suitable for picking up external noise bext with a transfer function Hbext. Hbext is the transfer function between the external surface of the cavity 12 where the external noise bext is applied and the external microphone 41, as shown in FIG. 1.

In the external processing chain 40, the external microphone 41 is connected via an analogue/digital converter 42 to an external processing filter 44, the output of which is connected to the summing unit 38.

The summing unit 38 thus ensures that the noise-canceling signals produced at the output of the filters 34 and 44 and the equalised music signal to be reproduced from the input 22 are routed to the amplifier 18 via the analogue/digital converter 20.

The filters and equalisers described here are digital filters implemented in a digital signal processor (DSP).

In particular embodiments, the headset 10 has both internal 30 and external 40 noise-canceling chains or either the internal 30 or external 40 noise-canceling chain is omitted and only one of the two microphones and associated filters is retained.

In any embodiment and according to the invention, the external 34 and internal 44 noise-cancelling filters, when present, have a transfer function each formed by the product of:

the inverse of the transfer function of a processed secondary path, and a noise cancellation transfer function.

The transfer function of the processed secondary path is the transfer function of the secondary path combined with the transfer functions of the various components providing processing up to the transducer 16, with the exception of the internal 34 or external 44 processing filter, as the case may be. These include the transfer functions of the microphone 31 or 41 as the case may be, the analogue/digital converter 32 or 42 as the case may be and the digital/analogue converter 20. The amplifier 18 is assumed to be unitary and if not, its transfer function is also integrated into the transfer function of the processed secondary path.

The inverse of the transfer function of the processed secondary path is applied by a stabilisation filter labelled 34A and 44A for the filters 34 and 44 respectively. These filters 34A, 34B have a stabilising transfer function denoted HFBcorr and HFFcorr respectively.

Each stabilisation filter 34A, 44A is followed at the output in the processing filter 34, 44 respectively by a noise cancellation filter 34B, 44B whose transfer function is denoted HFB2, HFF2 respectively.

The digital filters 34A, 44A and 34B, 44B used are, for example, infinite impulse response (IIR) or finite impulse response (FIR) filters.

The construction and nature of the filters 34 and 44 will now be described.

The residual noise received by the eardrum of the headset wearer, assumed to correspond to the sound picked up by the internal microphone 31, is denoted s.

HPA is the transfer function s/bext in the absence of active noise reduction, i.e. it is the passive attenuation of the cavity, bext being the ambient noise on the outer envelope of that cavity.

This HPA transfer function is usually close to a low-pass filter, which means that the structure forming the cavity mainly reduces high frequencies.

The residual noise s is expressed, in the Laplace domain, by the following expression:

$$s(p)=1/(1-\mathrm{PlantFB}*\mathrm{HFB}*\exp(-pT_{FB})*\exp(-pD_{FB}))*(\mathrm{HPA}+\mathrm{PlantFF}*\mathrm{HFF}*\exp(-pT_{FB})*\exp(-pD_{FF})*\mathrm{Hbext})*\mathrm{bext} \quad \text{[Math 1]}$$

Where:

p: a complex variable

HFB: transfer function of filter 34

HFF: transfer function of filter 44

HPA: transfer function of the passive attenuation of the headset structure bounding the cavity 12

Hbext: transfer function between the external surface of the cavity 12 where the external noise bext and the external microphone 41 are applied PlantFB=Gadci*Gdac*Hmici*Ha is the transfer function of the processed secondary path taken through the internal noise-cancelling processing chain 30

PlantFF=Gadce*Gdac*Hmice*Ha is the transfer function of the processed secondary path taken through the external noise-cancelling processing chain 40

Where:

Gadci and Gadce: gains of the analogue/digital converters 32 and 42 for the internal 31 and external 41 microphones respectively Gdac: output gain of the digital/analogue converter 20

Hmici: transfer function of the internal microphone 31

Hmice: transfer function of the external microphone 41

Ha: transfer function between the transducer 16 and the eardrum assumed to correspond to the measurement point of the internal microphone 31

Ha depends on the characteristics of the transducer, as well as the acoustic architecture around it, including the chambers in front of and behind the transducer when it is a loudspeaker.

Ha represents the transfer function of the secondary path, i.e. the transfer function between the transducer 16 and the point of positioning of the internal microphone 31 or the eardrum without taking delays into account. In the modelling, the propagation time of the acoustic wave was isolated in a specific term $\exp(-pT_{FB})$. Thus, the complete transfer function Hareal is expressed taking into account this delay as Hareal=Ha*$\exp(-pT_{FB})$.

$T_{FB}$: propagation time of the acoustic wave over the distance $d_{FB}$ between the transducer 16 and the internal microphone 31, TFB=$d_{FB}/c$, where c is the speed of sound (342 m/s)

$D_{FB}$: processing delay between the input and output of the digital signal processor for the internal noise-canceling processing chain 30

$D_{FF}$: processing delay between the input and output of the digital signal processor for the external noise-canceling processing chain 40

A first embodiment is now considered, in which the external noise-canceling processing chain 40 is omitted.

In this case, the residual noise s is expressed at the eardrum as:

$$s(p)=1/(1-\mathrm{PlantFB}*\mathrm{HFB}*\exp(-pT_{FB})*\exp(-pD_{FB}))*(\mathrm{HPA})*\mathrm{bext} \quad \text{[Math 2]}$$

It is measured and processed from the internal microphone 31 alone.

As the filter 34 is formed of two parts, namely a noise cancellation filter 34B with transfer function HFB2 and the stabilisation filter 34A with transfer function HFBcorr, we have: HFB=HFBcorr*HFB2

According to the invention, the transfer function HFBcorr is taken to be substantially equal to the inverse of the transfer function of the processed secondary path PlantFB, i.e.:

$$\mathrm{HFBcorr}*\mathrm{PlantFB}\sim=1 \quad \text{[Math 3]}$$

The stabilisation filter 34A is then constructed to substantially apply this transfer function HFBcorr~=$\mathrm{PlantFB}^{-1}$.

To construct the filter 34A, the transfer function PlantFB of the processed secondary path is first measured on a full headset but without programming the internal processing filter 34 in the digital signal processor (DSP) by exciting the transducer 16 with a sine function of variable frequency over the entire audio range and measuring the signal obtained by an artificial ear 14, thus determining the value of Ha. The values of the other terms are known, these being the transfer functions of documented commercial components.

The inverse $\mathrm{PlantFB}^{-1}$ of this transfer function is then calculated numerically.

Since the PlantFB transfer function does not integrate the delays $\exp(-pT_{FB})$ and $\exp(-pD_{FB})$, it is invertible and its inverse being causal can be realised by a filter in a real-time system. Therefore, delays are not taken into account in the transfer function of the processed secondary path. Otherwise, the delay terms would be invertible but would not allow the construction of a filter implementing its inverse in a real-time system, which would then have to be anti-causal.

A stabilisation filter 34A is then constructed, with a transfer function HFBcorr that reproduces the $\mathrm{PlantFB}^{-1}$ transfer function as closely as possible.

In practice, the stabilisation filter 34A is constructed so that its transfer function is substantially equal to the inverse of the transfer function of the processed secondary path, along the entire audio range, and particularly from 5 Hz to 50 Hz and from 1 kHz to 10 kHz, to within 5 dB, advantageously 1 dB, of gain and with a phase shift of +45 to −45° on the corrected phase of the linear phase due to the pure delay resulting from propagation in air and the delay due to the processor.

The filter is programmed and implemented in the digital signal processor (DSP). This is advantageously achieved by a combination of several cascaded filters.

The action of the stabilisation filter 34A applies over the entire frequency range allowed by the sampling frequency (Fs) of the digital signal processor (DSP). For example, if Fs=384 kHz, the correction range of the 34A filter is 0 Hz to 192 kHz.

The second part of the filter 34, consisting of the noise cancellation filter 34B with transfer function HFB2, is designed to ensure stability at all frequencies, while applying the highest possible gain in the audio band, namely above 20 dB to provide maximum noise cancellation performance. The filter 34B is advantageously formed by a proportional integral (PI) filter or a shelving filter.

As the residual noise of the internal noise-canceling processing chain 30 with only the internal microphone 31 is:

$$s(p)=1/(1-\mathrm{PlantFB}*\mathrm{HFB}*\exp(-pT_{FB})*\exp(-pD_{FB}))*(\mathrm{HPA})*\mathrm{bext} \quad \text{[Math 2]}$$

Incorporating [Math 3] into [Math 2], we get:

$$s(p)\sim=1/(1-\mathrm{HFB2}*\exp(-pT_{FB})*\exp(-pD_{FB}))*(\mathrm{HPA})*\mathrm{bext}.$$

It is understood that the phase of the denominator is only dependent on a pure delay, which is the sum of the time $T_{FB}$ of the physical propagation of the acoustic wave and the time $D_{FB}$ of the DSP processing, and on the phase of the HFB2 noise cancellation filter pushing back into the frequency band a cancellation of the denominator, which is the cause of the audible feedback. This is avoided, even if the noise suppressor has a high gain over a wide frequency range.

Figure 2:
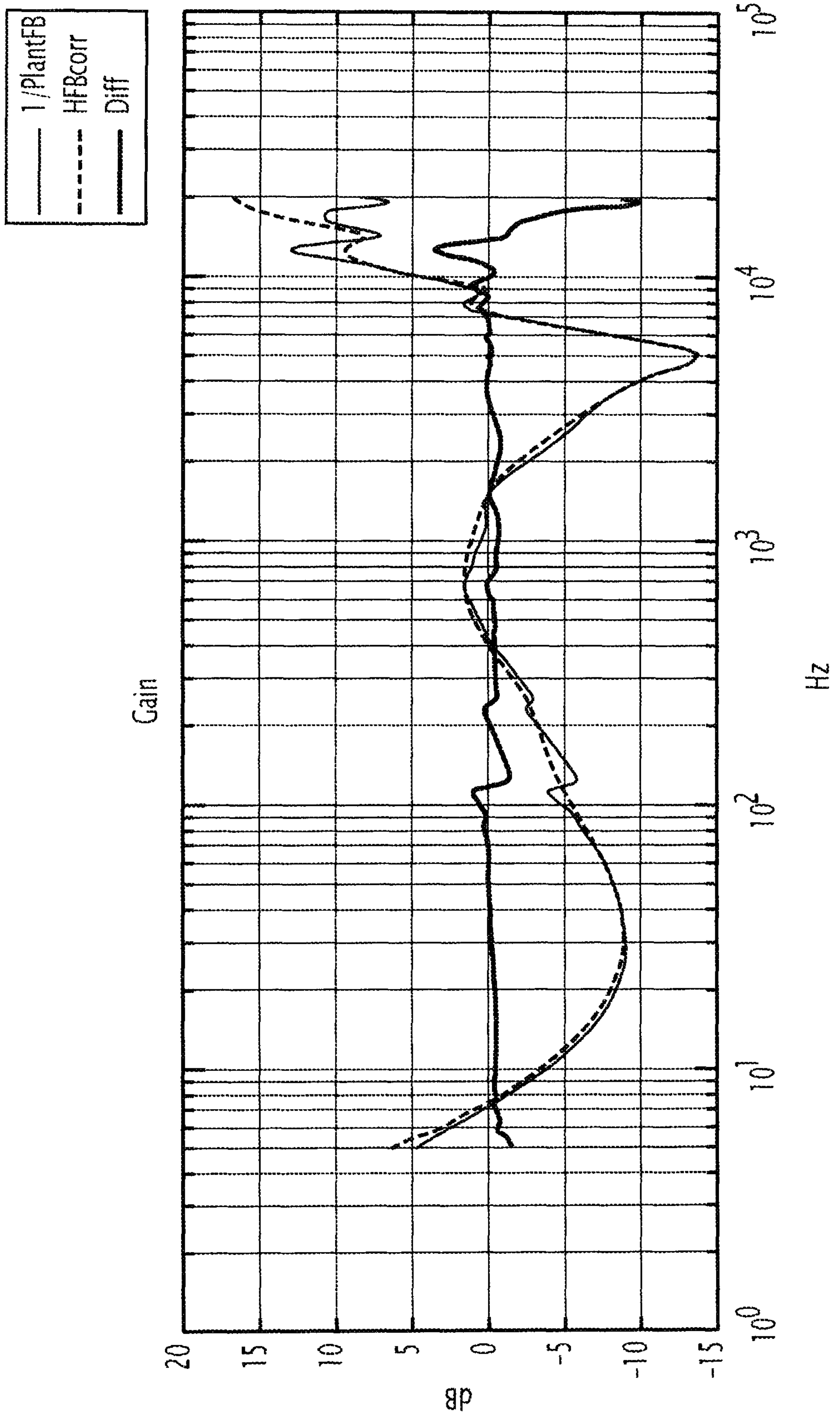
FIG. 2 is a curve showing, as a function of frequency, the gains of the inverse of the transfer function of the processed secondary path, the stabilisation filter and the combination of the transfer function of the processed secondary path and the stabilisation filter.
Figure 3:
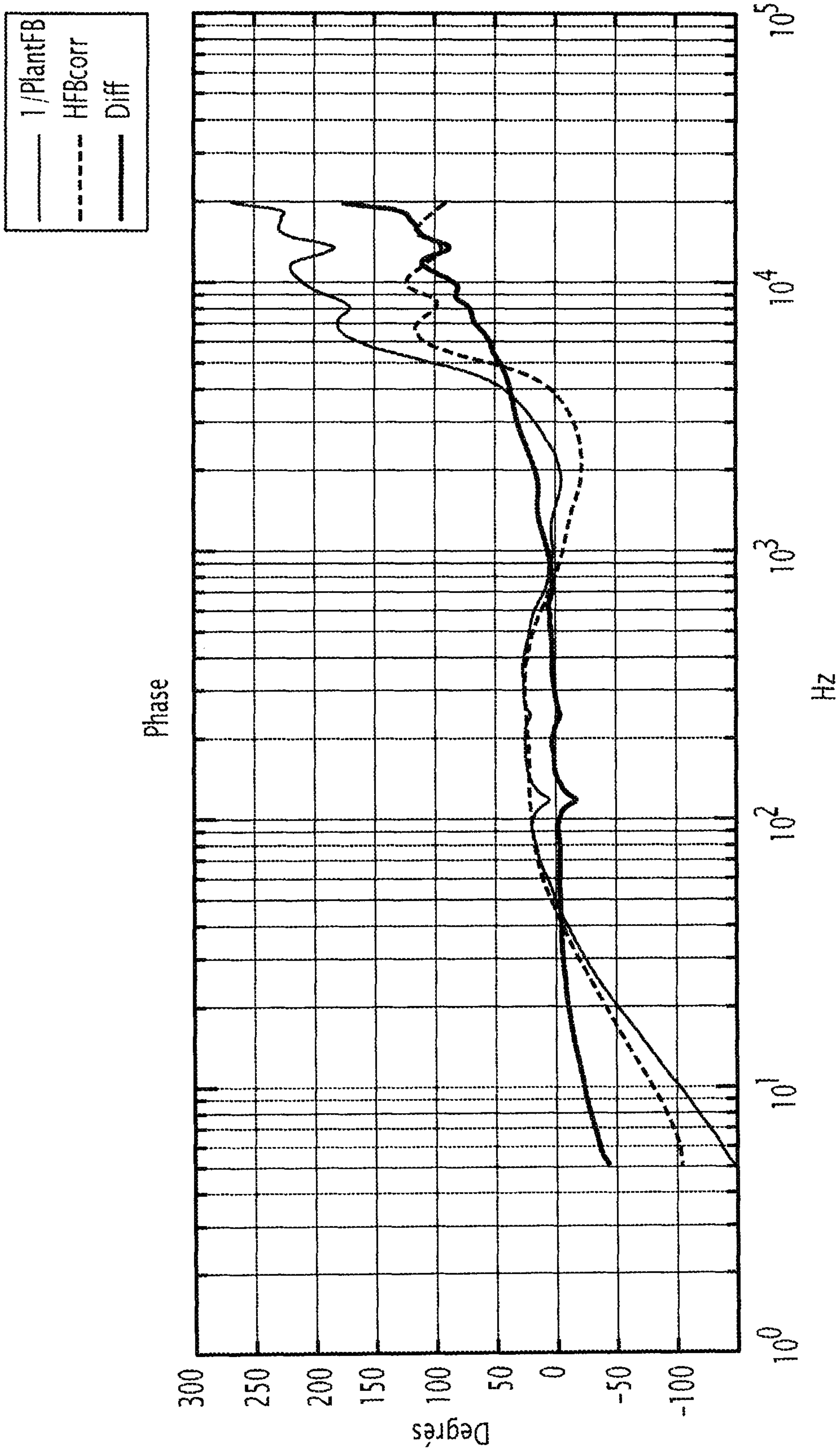
FIG. 3 is a curve showing the phases of the same quantities as in FIG. 2 as a function of frequency.

The result is depicted depicted in FIGS. 2 and 3.

In these figures, the inverse of the transfer function $PlantFB^{-1}$ is shown as a thin solid line. It is the exact mathematical inverse of the transfer function PlantFB measured experimentally on the headset.

The actual transfer function HFBcorr of the implemented stabilisation filter 34A is shown as a dashed line. These two curves are very close as explained above.

Thus, the difference equal to PlantFB*HFBcorr shown in bold solid line corresponds to a practically flat transfer function in terms of gain (FIG. 2) and phase (FIG. 3), the phase difference at high frequencies being mainly due to pure delays of the system, when considering:

$D_{FB}$=11 μs $T_{FB}$~=6 μs

A second embodiment is now considered, in which the internal noise-canceling processing chain 30 is omitted and only the external noise-canceling processing chain 40 is present.

In this case, the residual noise s is expressed at the eardrum as:

$$s(p)=(HPA+PlantFF*HFF*\exp(-pTFB)*\exp(-pDFF)*Hbext)*bext \quad \text{[Math 4]}$$

It is measured and processed from the external microphone 41 alone.

Similarly for the external noise-canceling processing chain 40, the noise cancellation filter 44B having a transfer function denoted HFF2 and the stabilisation filter 44A having a transfer function HFFcorr, we have: HFF=HFFcorr*HFF2

According to the invention, the transfer function HFFcorr is taken to be substantially equal to the inverse of PlantFF, so that:

$$FFcorr*PlantFF\sim=1 \text{ i.e. } HFFcorr\sim=PlantFF^{-1}. \quad \text{[Math 5]}$$

In this case, the secondary path processed is given by:

$$PlantFF=Gadce*Gdac*Hmice*Ha$$

To construct the filter 44A, the transfer function PlantFF of the processed secondary path is first measured on a full headset in the absence of the internal processing filter 44 by subjecting the transducer 16 to a variable frequency sweeping the audio range and measuring the signal obtained by an artificial ear 14

The inverse $PlantFF^{-1}$ of this transfer function is then calculated numerically. In practice, the stabilisation filter 44A is constructed so that, as in the previous embodiment, its transfer function is substantially equal to the inverse of the transfer function of the secondary path, from 5 Hz to 50 Hz and from 1 kHz to 10 kHz, and advantageously over the whole audio range, to within 5 dB, advantageously 1 dB, of the gain, and with a phase shift of +45 to −45° on the phase without taking into account the linear phase due to the pure delay resulting from propagation in air and from the delay due to the processor.

The residual noise is for the single external noise-canceling processing chain 40 with only the external microphone 41 written as:

$$s(p)=(HPA+PlantFF*HFF*\exp(-pT_{FB})*\exp(-pD_{FF})*Hbext)*bext \quad \text{[Math 4]}$$

Incorporating [Math 5] into [Math 4], we get:

$$s(p)=(HPA+HFF2*\exp(-pT_{FB})*\exp(-pD_{FF})*Hbext)*bext$$

This form allows the filter HFF2 to be defined without having to take into account any constraints on the other elements of the system, these being reduced in the above expression to a simple delay $\exp(-pT_{FF})*\exp(-pD_{FF})$.

The optimal transfer function filter 44, denoted HFFopt, corresponding to the residual noise cancellation expressed by [Math 4] is:

$$HFFopt=-(HPA/Hbext)/(PlantFF)*\exp(-pT_{FB})*\exp(-pD_{FF})$$

The noise cancellation filter 44B is chosen so that its transfer function is equal to HFF2=−HPA/Hbext, so that the residual noise is:

$$s(p)=HPA*(1-\exp(-pT_{FB})*\exp(-pD_{FF}))*bext$$

Since the $T_{FB}$ and $D_{FF}$ delays are small, the product of the two exponentials −exp(−pTFB)*exp(−pDFF) is close to 1 over a wide frequency range, so that (1−exp(−pTFB)*exp(−pDFF)) is very close to zero, which corresponds to very high noise attenuation over a wide frequency range.

A third embodiment is now considered in which both the internal noise-canceling processing chain 30 and the external noise-canceling processing chain 40 are present.

The residual noise s is expressed, in the Laplace domain, by the expression:

$$s(p)=1/(1-PlantFB*HFB*\exp(-pT_{FB})*\exp(-pD_{FB}))*(HPA+PlantFF*HFF*\exp(-pT_{FB})*\exp(-pD_{FF})*Hbext)*bext \quad \text{[Math 1]}$$

In this case, as before, the transfer functions of the processing filters 34 and 44 are expressed as:

HFB=HFBcorr*HFB2 with HFBcorr constructed such that HFBcorr*PlantFB~=1 and

HFF=HFFcorr*HFF2 with HFFcorr constructed such that HFFcorr*PlantFF~=1

The residual noise s is then written:

$$s(p)=1/(1-HFB2*\exp(-pT_{FB})*\exp(-pD_{FB}))*(HPA+HFF2*\exp(-pT_{FB})*\exp(-pD_{FF})*Hbext)*bext \quad \text{[Math 6]}$$

and advantageously by choosing HFF2=−HPA/Hbext as explained above, we have:

$$s(p)=1/(1-HFB2*\exp(-pT_{FB})*\exp(-pD_{FB}))*HPA*(1-\exp(-pT_{FB})*\exp(-pD_{FF}))*bext$$

In this embodiment, the advantages of both previous embodiments are combined.

The invention claimed is:

1. Noise canceling headphones comprising:

an electro-acoustic transducer placed in a sound reproduction cavity;

at least one noise-canceling processing chain comprising:

a microphone to capture ambient sound;

a noise-canceling filter to process a signal from the microphone to produce a noise-canceling signal;

means for applying the noise-canceling signal to drive the electro-acoustic transducer;

wherein, for the or each noise-canceling processing chain, the noise-canceling filter comprises in series:

a stabilisation filter whose transfer function is substantially equal to the inverse (HFBcorr, HFFcorr) of a transfer function of a processed secondary path (Plant FB, Plant FF), and a noise cancellation filter whose transfer function is a noise cancellation transfer function (HFB2, HFF2), the secondary path being formed between the electro-acoustic transducer and a user's eardrum, and the transfer function of the processed secondary path being the transfer function of the secondary path combined with a transfer functions of various components providing processing up to the transducer in the noise-cancellation processing chain, except for the noise-canceling filter, wherein the noise-canceling headphones further comprise an external noise-cancellation processing chain with an external microphone placed in the sound reproduction cavity; and wherein in the external noise-cancellation processing chain, a noise cancellation transfer function (HFF2) is substantially equal to the opposite of the quotient of a transfer function corresponding to a passive attenuation of the cavity and a transfer function between an outer envelope of the cavity and the external microphone.

2. Noise-canceling headphones according to claim 1, wherein the stabilisation filter is constructed so that its transfer function (HFBcorr, HFFcorr) is substantially equal to the inverse of the transfer function of the processed secondary path (Plant FB, Plant FF), from 5 Hz to 50 Hz and from 1 kHz to 10 kHz, to within 5 dB of gain and with a phase shift of +45 to −45° on the corrected phase of the linear phase due to the pure delay resulting from propagation in air and from the delay due to the processor.

3. Noise-canceling headphones according to claim 1, wherein the noise-canceling headphones further comprise an internal noise-canceling processing chain having an internal microphone placed in the sound reproduction cavity.

4. Noise canceling headphones according to claim 3, wherein in the internal noise cancelling processing chain, the noise cancelling transfer function (HFB2) has a gain greater than 20 dB over the entire audio range.

5. Noise-canceling headphones according to claim 3, wherein in the internal noise-processing chain, the stabilisation filter is a proportional integral filter or a shelving filter.

* * * * *